United States Patent
Deegan et al.

(10) Patent No.: US 6,546,781 B1
(45) Date of Patent: Apr. 15, 2003

(54) METHOD OF VERIFYING SPINDLE BEARING FUNCTIONALITY PRIOR TO SERVICE

(75) Inventors: Michael David Deegan, Farmington Hills, MI (US); Ming Loo, Ann Arbor, MI (US)

(73) Assignee: Ford Motor Company, Dearborn, MI (US)

( * ) Notice: Subject to any disclaimer, the term of this patent is extended or adjusted under 35 U.S.C. 154(b) by 70 days.

(21) Appl. No.: 09/679,670

(22) Filed: Oct. 5, 2000

(51) Int. Cl.[7] .............................................. G01N 29/00
(52) U.S. Cl. ........................... 73/1.82; 73/593; 73/659; 73/660
(58) Field of Search ................................ 73/1.82, 1.84, 73/11.01, 593, 659, 660, 663, 579

(56) References Cited

U.S. PATENT DOCUMENTS

| | | | | |
|---|---|---|---|---|
| 4,519,734 A | * | 5/1985 | Mitchell et al. | 409/231 |
| 4,744,242 A | * | 5/1988 | Anderson et al. | 73/104 |
| 4,829,815 A | * | 5/1989 | Kuzas | 73/146 |
| 5,187,434 A | * | 2/1993 | Ando | 324/207.25 |
| 5,663,894 A | * | 9/1997 | Seth et al. | 73/654 |
| 5,921,731 A | * | 7/1999 | Chandrasekar | 409/231 |
| 6,081,057 A | * | 6/2000 | Tanaka et al. | 310/90 |
| 6,116,089 A | * | 9/2000 | Ellbiary et al. | 73/593 |

* cited by examiner

Primary Examiner—Daniel S. Larkin
Assistant Examiner—Jacques Saint-Surin
(74) Attorney, Agent, or Firm—Damian Porcari

(57) ABSTRACT

A method of verifying spindle bearing functionality prior to service, comprising: assembling a machine-tool spindle having an outer housing rotatably supporting an inner spindle shaft about a spindle axis by use of roller bearing sets, at least one set being compressed along the spindle axis to promote a resilient bearing preload force between the housing and shaft; suspending the housing of said assembly on a non-resonating flexible support, the spindle shaft being essentially isolated from the housing except for the preloaded rolling bearing set; sharply striking the inner spindle shaft along said spindle axis to induce an axially oscillating frequency; measuring the oscillating frequency in the shaft as it is affected by the degree of bearing preload of such at least one bearing set; and comparing the measured induced frequency to a known frequency analysis for the type of spindle assembly which is correlated to varying bearing preloads, the comparison indicating the spindle bearing functionality prior to service.

8 Claims, 4 Drawing Sheets

(1) $f_n = 1/2\pi \sqrt{K_a / (Mm/M+m)}$ (2) $\delta_a = BD \sin(\alpha - \alpha_0) / \cos\alpha$ (3) $F_a / ZD^2\alpha = \sin\alpha [(\cos\alpha_0 / \cos\alpha) - 1]^{1.5}$ (4) $K_a = dF_a / d\delta_a = dF_a / d\alpha * d\alpha / d\alpha_a$ and
$K_a = ZDK/B\cos\alpha_0 [(\cos\alpha_0 / \cos\alpha) - 1]^{1/2} [\cos^3\alpha (\cos\alpha_0 - \cos\alpha) + 1.5 \sin^2\alpha]$ (5) $\alpha^1 = \alpha + \{(F_a / ZD^2\alpha) - \sin\alpha [(\cos\alpha_0 / \cos\alpha) - 1]^{1.5}\} / \{\cos\alpha [(\cos\alpha_0 / \cos\alpha) - 1]^{1.5} + 1.5 \tan^2\alpha [(\cos\alpha_0 / \cos\alpha) - 1]^{0.5} \cos\alpha_0\}$
until $\alpha^1 - \alpha$ is essentially Zero

FIG. 3

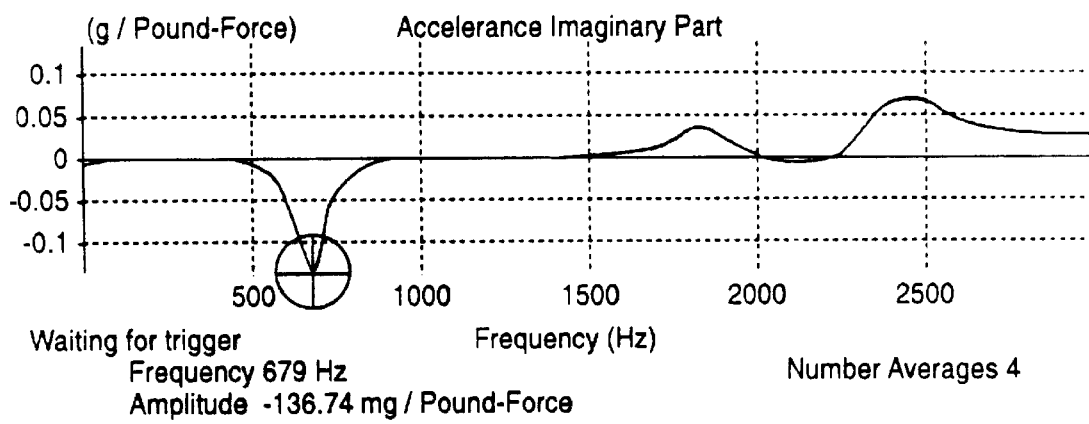

Waiting for trigger
Frequency 679 Hz
Amplitude -136.74 mg / Pound-Force
Number Averages 4

FIG. 5

METHOD OF VERIFYING SPINDLE BEARING FUNCTIONALITY PRIOR TO SERVICE

BACKGROUND OF THE INVENTION

1. Technical Field

This invention relates to technology for assembling and operating machine tool spindles using rolling bearings (at least certain of which are preloaded), and, more particularly, to techniques for verifying the accuracy of pre-loading and/or other settings of the bearings.

2. Discussion of the Prior Art

Properly assembled machine tool spindles, such as for boring and milling, have a designed axial bearing stiffness, which, if adhered to, provides a useful life of at least about 5000 hours before maintenance steps are undertaken to readjust the spindle bearings. Unfortunately, common assembly problems do affect bearing preloads, such as: (i) improper fitting or misalignment of either the outer bearing race rings into the housing bore or the inner bearing race rings onto the spindle shaft, (ii) presence of foreign particles in or about the race rings, and (iii) operator skill in wrongly controlling compression to obtain the preload as a result of torquing a locknut. If such problems are not detected prior to putting the spindle into service, it will have a useful life shortened to 25 hours or less, and often irreparable damage is done requiring replacement of bearings or other components.

What is needed is a method that enables plant personnel to quickly test and determine bearing preload conditions and other bearing settings to see if they all fall within specific designed parameters, thus preventing premature spindle failure and enhancing spindle reliability.

The inventors are unaware of any known method to perform verification of proper bearing preloads prior to the spindle being used in service. Commercial manufacturers of spindles may only subject their spindles to a test using an axially applied hydraulic force that moves the spindle shaft to test whether the outer race rings have been properly locked up to the housing while the spindle housing is fixed or clamped. This test gives no information or indication as to the accuracy of preload of the spindle bearings.

SUMMARY OF THE INVENTION

Machine tool spindle assemblies have essentially two masses which are interconnected by a compressed spring in the form of rolling bearing sets. An outer mass is constituted essentially of the spindle housing along with any outer bearing races, while an inner mass is constituted of a solid spindle shaft with any secured inner bearing races. The invention has discovered a simple technique for quickly and reliably verifying bearing functionality and determining whether the bearing preloads are within a designed range. The technique relies upon supporting the outer mass on non-resonating flexible members, such as cloth straps or a soft foam; the outer mass is essentially environmentally isolated. A natural vibrating frequency of the inner mass is induced by sharply striking the end of the spindle shaft desirably in a centered axial direction. The tone or frequency of the axially oscillating inner mass moves in opposition to the suspended non-moving outer mass as modified by the degree of axial stiffness imparted through the preloaded bearings located between the masses. The induced frequency is immediately measured and used as a tool to verify the functionality of the spindle assembly.

The method steps of this invention, in one aspect, comprises: (a) assembling a machine tool spindle having an outer housing rotatably supporting an inner spindle shaft about a spindle axis by use of rolling bearing sets, at least one set being compressed along the spindle axis to promote a bearing preload force between the housing and shaft; (b) suspending the housing on a non-resonating flexible support with the spindle shaft essentially isolated from the housing with freedom to oscillate as modified by the preloaded rolling bearing set; (c) sharply striking the spindle shaft along the spindle axis to induce an oscillating frequency in the shaft that is affected by the degree of bearing preload of such at least one bearing set; and (d) measuring the induced frequency and comparing it to a known frequency analysis of such type of spindle assembly, the frequency analysis being correlated to varying bearing preloads so that the comparison will indicate spindle bearing functionality.

BRIEF DESCRIPTION OF THE DRAWINGS

FIG. 3 is a flow of mathematical steps used by the computer implemented frequency analyzer FIG. 5 is a graphical illustration of a signal sensed by the accelerometer in FIG. 2, the signal showing amplitude and frequency as indicators of front bearing preload and any rear bearing interference.

DETAILED DESCRIPTION AND BEST MODE

Figure 1:
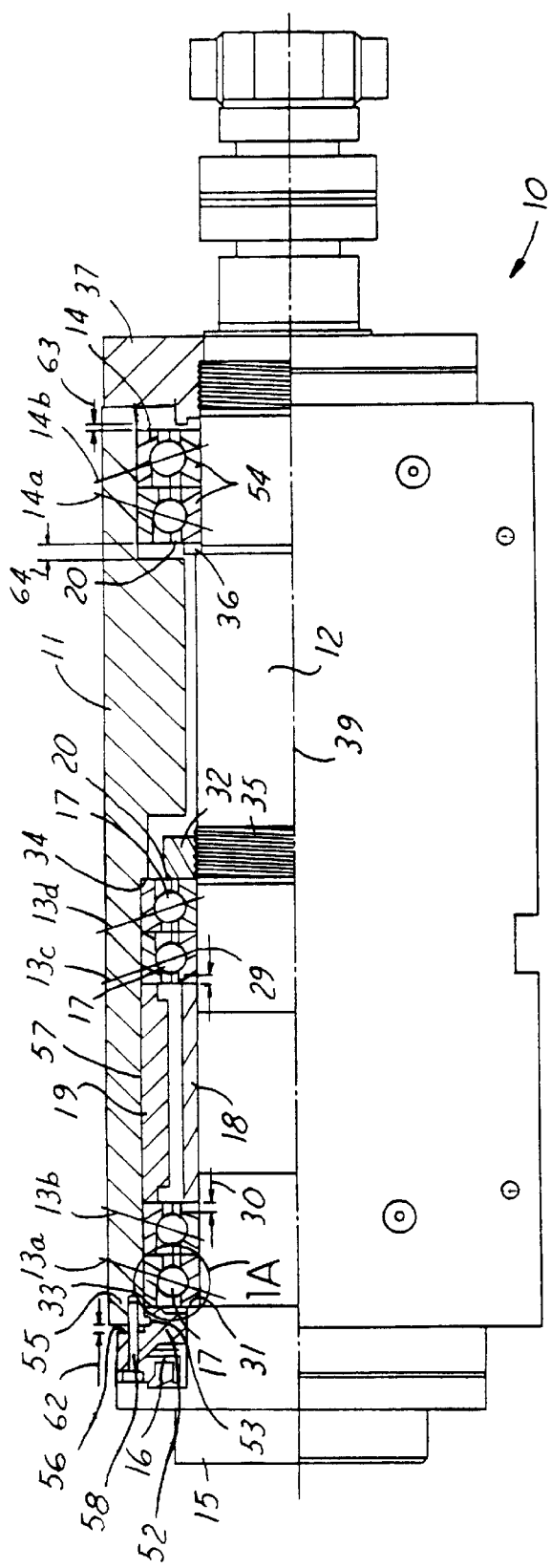
FIG. 1 is an elevational view, partly in section, of an assembled machine tool spindle that is to be subjected to the verification method of this invention.
Figure 1A:
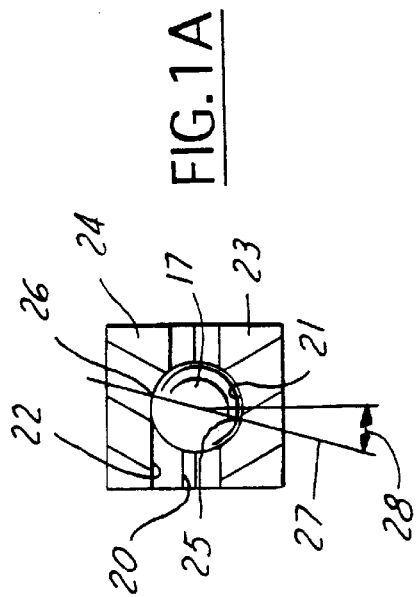
FIG. 1A is an enlarged view of a portion of FIG. 1 as circled.

As shown in FIG. 1, an assembled machine tool spindle comprises a sleeve-like housing 11 rotatably supporting a solid spindle shaft 12 therein by way of front bearing set 13 and rear bearing set 14. The working end 15 of shaft 12 (for carrying a boring or milling tool) is rotatably sealed to the end of the housing by seal element 16 and O-ring 53 carried by the front end cap 52; such sealing protects the bearing sets from contamination and may serve to retain air/lubricant mixtures inside the bearing sets. Front bearing set 13 has tandem rows 13a and 13b of ball bearings 17, separated from rows 13c and 13d of ball bearings by inner and outer spacer bushings 18, 19. The housing, shaft and ball bearing sets are comprised essentially of steel, but the ball bearings may be comprised of ceramics, such as silicon nitride, which are strong in compression.

Each ball bearing in a row is circumferentially spaced from adjacent ball bearings and cradled within annular cages 20. Each ball bearing engages contoured mating surfaces 21 on each inner race 23, and contoured mating surface 22 on each outer race 24; such engagements takes place at respective contact points 25, 26 which define a line 27 passing through such contact points at a contact angle 28 relative to a plane perpendicular to the shaft axis 39. Contact angle 28 for bearing rows 13c and 13d are the complementary equivalent opposite of the contact angles 28 for bearing rows 13a and 13b. An offset gap 29, 30 is introduced between the opposite ends of the inner spacer bushing and adjacent inner races to facilitate preloading; these offset gaps are normally toleranced on the order of 0.0001 inch and such accuracy is obtained by grinding. The front bearing set 13 is comprised of (a) caged rows of ball bearings 17, (b) an inner lateral stack consisting of inner races 23, an inner spacer bushing 18, two ground offset gaps 29 and 30, an annular front stop shoulder 31, and a threaded nut 32 acting as a stop at the other end, and (c) an outer lateral stack of outer races 24, outer spacer bushing 19 with no offset clearances or gaps except lock-up gap 62 (between the front end 55 of the housing and shoulder 56 on the front end cap 52), and shoulder stop 33 of the front end cap along with shoulder 34 in the interior bore surface 57 of the housing, at respectively opposite ends of the stack.

To preload the front bearing set 13, the bearing set has its inner bearing race rings 23 heated on an induction heating mandrel to thermally expand their inside diameters, allowing for ease of axial placement on shaft 12 as shown in FIG. 1. While the inner race rings are still warm, the entire inner bearing stack and portions of the outer bearing stack are axially slid onto the shaft 12. Then the inner lateral stack is compressed by nut 32 as it is threaded onto a threaded portion of the shaft at location 35. The axial reaction force of the stop 31 and the advancing axial force of the nut 32 will concurrently squeeze the inner races together from opposite ends, taking the slack up provided by the off-set clearances 29, 30. The contact angles 28 of the ball bearing rows become slightly increased and the lines 27 become more slanted. The ball bearings become compressed between the surfaces 21 and 22 of the inner and outer races respectively and become slightly distorted or flattened at the contact points. With the inner lateral stack now axially clamped, the housing is slid onto front bearing set 13 allowing for the outer lateral stack to be clamped or locked-up by using cap screws 58 to tighten the front end cap 52 to the front end 55 of the housing, causing the gap 62 to be reduced and forcing the outer races to be clamped between the shoulder stop 33 on the front end cap and shoulder 34 at the other end of the stack. The front bearing set 13 is designed to be preloaded to a specific degree and this is obtained by controlling the degree of torquing of threaded nut 32 to take up the ground-in gaps 29,30.

The rear bearing set 14 is of similar construction and is slid into place after the housing has been placed on the preloaded front bearing set. The rear bearing set is similarly preloaded on the inner races 54 by threadably tightening rear-end cap 37 to move the inner races against annular shoulder stop 36. The outer races must be free to slide axially in the housing bore to accommodate any axial differential thermal expansion between the shaft and the housing. Thus, there is no lock-up of the outer races as shown in FIG. 1 due to the gaps 64 and 63.

Proper preloading of the front bearing set 13 can be distorted by any number of assembly factors, such as improper torquing of the threaded nut (which usually requires only five degrees of rotation when strong threads are used), out of squareness of the locknut, improper interference fitting or cocking of the races into the housing bore or onto the shaft outer surface, and foreign particles contaminating the inter-engaging surfaces. Verification of the proper bearing preload is extremely desirable if the spindle is to have a more assured long life.

Figure 2:
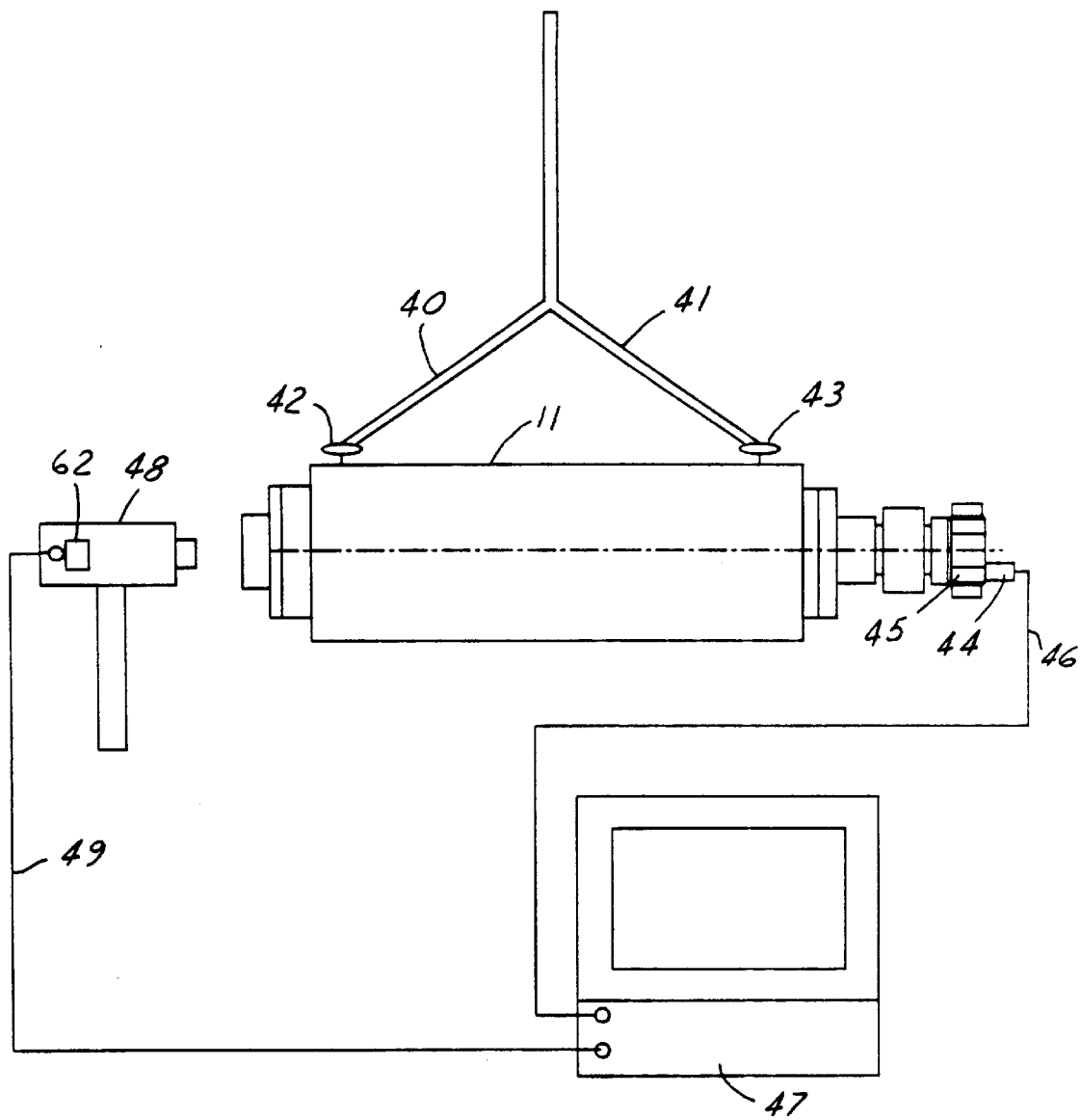
FIG. 2 is a schematic illustration of apparatus components used to carry out the verification method on the spindle of FIG. 1 according to this invention.

As shown in FIG. 2, the housing 11 must be essentially isolated from external masses for the test to take place. This is accomplished by suspending the housing 11 on non-resonating support elements, such as a pair of cloth straps 40, 41 which are connected to ring fasteners 42, 43 on opposite ends of the housing. The shaft becomes essentially isolated for oscillating movement except as restrained by the axial stiffness imparted by the preloaded front bearing 13; the rear bearing set 14 should offer little or no restriction to axial movement of the shaft since it is designed to be free to slide slightly for accommodating axial thermal expansion.

An accelerometer or axial frequency sensor 44 is attached to the shaft end 45 and has a wire 46 connected to a computer implemented frequency analyzer 47 to transfer a frequency signal thereto. A hammer 48 (having a force sensor 62 mounted thereon) is connected by wire 49 to the analyzer 47 for conveying an impact signal. The hammer is used to strike a sharp impact blow to the shaft. The test is initiated by a blow of the hammer 48, desirably impacting a centered axial blow on the end of the spindle shaft 15. This blow must induce a natural oscillating frequency within the inner mass of the spindle assembly, which frequency is modified essentially only by the axial stiffness of the preloaded front bearing set 13.

The signal is sent to the analyzer 47, measured and compared to stored or known frequency data for the same type of spindle assembly, the data being correlated to varying preload stiffnesses over a range greater than that designed for the assembly. The known or stored frequency data is gathered by use of a computer implemented analytical dynamic math model 51 as shown in FIG. 3. The axial spindle frequency $f_n$ is calculated for varying preload forces by the relationship $$(1)\ f_n = (1/2\pi) * (k_a/(Mm/M + m))^{0.5}$$

(Mm/(M+m)) is equivalent mass, where m=inner mass, M=outer mass, and $k_a$ represents the axial bearing stiffness which in turn is calculated as a function of bearing preload force $dF_a$ and bearing axial deflection $d\delta_a$. The axial stiffness $k_a$ depends upon the contact angle of the ball bearings with their races within a single row; thus, for a single row angle $\alpha_0$, that increases to $\alpha_1$ under an applied centric axial preload $F_a$ and the bearing deflecting axially an amount $\delta_a$, the following relationships can be used:

$$\delta_a = BD\ \sin(\alpha - \alpha_o)/\cos \alpha \tag{2}$$

$$F_a/ZD^2K = \sin \alpha[(\cos \alpha_0/\cos \alpha) - 1]^{1.5} \tag{3}$$

$$k_a = dF_a/d\delta_a = dF_a/d\alpha \cdot d\alpha/d\ \delta_a\ \text{and} \tag{4}$$

$$k_a = ZDK/B\ \cos \alpha_0[(\cos \alpha_0/\cos \alpha) - 1]^{1/2}[\cos^3 \alpha(\cos \alpha_0 - \cos \alpha) + 1.5 \sin^2 \alpha]$$

Where B is the total curvature of the ball and inner and outer race configuration K is an axial deflection constant dependent on bearing material and total curvature B D is the diameter of the ball, and Z is the number of balls.

These equations may be iterated for new contact angles under new loads to obtain different preloads or axial stiffness rendering different frequencies. Typically the equations may be solved numerically by the Newton-Raphson method. The equation to be satisfied for such iteration is:

$$(5)\ \alpha^1 = \alpha + \{(F_a/ZD^2K) - \sin\alpha[(\cos\alpha_0/\cos\alpha) - 1]^{1.5}\}/$$
$$\{\cos\alpha[(\cos\alpha_0/\cos\alpha) - 1]^{1.5} +$$
$$1.5\tan^2\alpha[(\cos\alpha_0/\cos\alpha) - 1]^{0.5}\cos\alpha_0\}$$
$$\text{until } \alpha^1 - \alpha \text{ is essentially zero.}$$

The quickness and reliability of this verification procedure is extremely helpful in working with rebuilt spindle assemblies when the preload is to be set and adjusted to exactly the original design preload with little difficulty.

Figure 4:
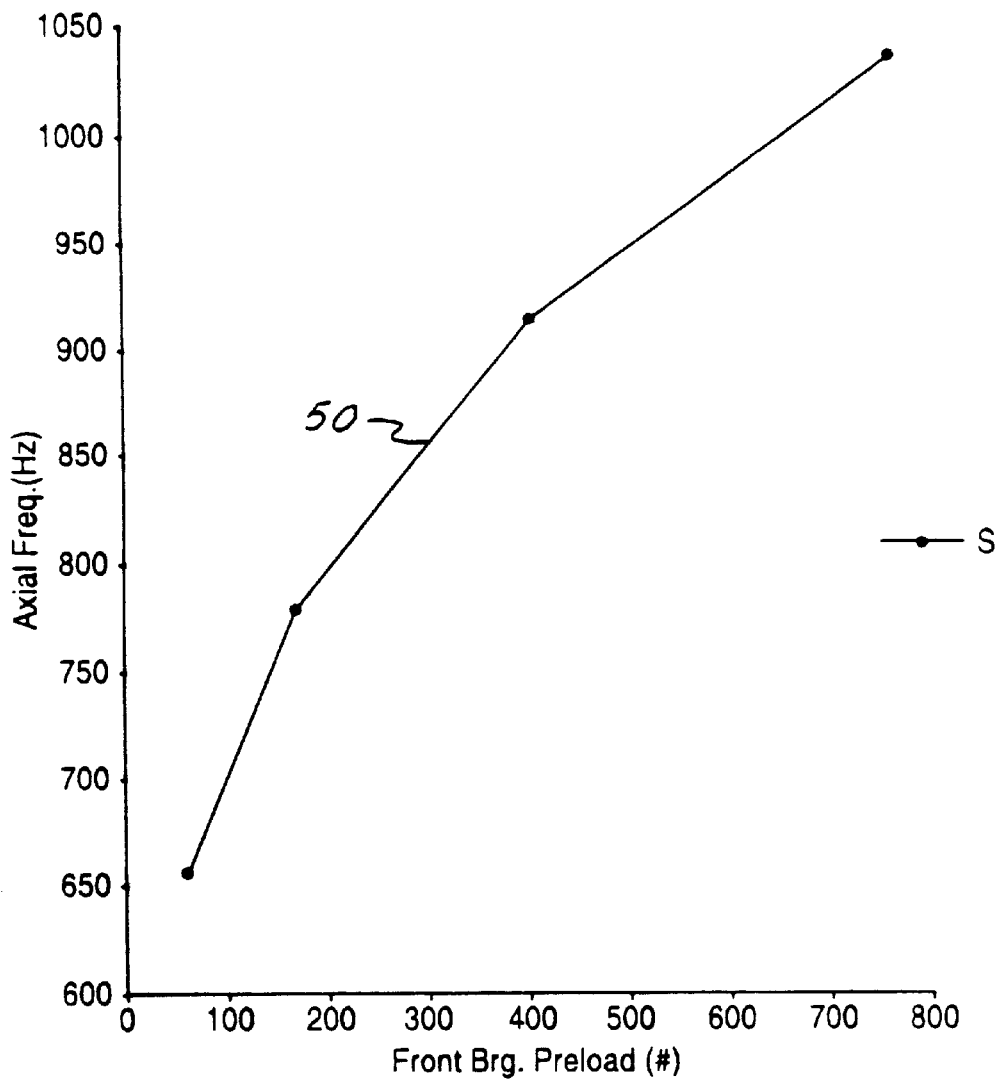
FIG. 4 is a graphical illustration showing frequency data collected by the computer implemented analyzer of FIGS. 2 and 3, such data being plotted as a function of bearing preload force.

By iterating such calculations for a broad range of preload forces and/or deflections, a plot, 50, of frequency (Hz) as a function of preload force (lbs) can be obtained as shown in FIG. 4. The operator of the test apparatus can then determine where the measured frequency signal intercepts the plot 50 for revealing, by interpolation, the real or existing preload force of the spindle under test. Measured test frequencies that fall outside the designed range (typically 550–650 Hz) of the plot, would indicate, for example, if at the plot's low-end (below 550 Hz), insufficient tightening torque on the locknut in the assembly of the spindle, and if at the high end, it indicates the rear bearing set is unable to slide in the housing bore due to cocking or misalignment (as shown as a blip in FIG. 5), or excessive front bearing axial preloading.

While the best mode and viable alternatives for carrying out the invention have been described in detail, those familiar with the art to which this invention relates will recognize various alternative designs and variations for the practicing the invention as defined by the following claims.

We claim:

1. A method of verifying spindle bearing functionality prior to service, said spindle having been assembled with a housing about a shaft carrying one or more bearing sets axially compressed to exert a preload force between the housing and shaft, comprising:
   (a) suspending the housing of said assembly on an essentially non-resonating support allowing said shaft and said housing the freedom to oscillate except as modified by the preloaded bearing force there-between;
   (b) sharply striking the end of the shaft to induce its natural vibration frequency as modified by the degree of axial bearing preload stiffness between said housing and shaft; and
   (c) measuring said induced frequency and comparing it to known frequency data for said type of spindle assembly correlated to varying bearing preload stiffnesses, where said known frequency data is gathered by use of a computer implemented analytical dynamic model wherein axial spindle frequency is calculated for varying bearing preloads by the relationship $F_a = \frac{1}{2}\pi\sqrt{k_a/Mm/M+m}$, with M being the outer mass, m being the inner mass, and $k_a$ being axial stiffness calculated as a function of bearing preload force and bearing axial deflection.

2. The method as in claim 1, in which said comparison is carried out by plotting said frequency data as a function of preload forces and determining where the measured frequency intercepts said plot for revealing the existing preload condition.

3. A method of verifying spindle bearing functionality prior to service, comprising:
   (a) assembling a machine-tool spindle having an outer housing rotatably supporting an inner spindle shaft about a spindle axis by use of a front bearing set located on said shaft and adjacent to the working end of said shaft, and a rear bearing set located remote from said working end of the shaft, whereby the front bearing set is provided with a bearing preload while the rear bearing set is free to slide within the housing absent any preload there-between;
   (b) suspending the housing of said assembly on a non-resonating flexible support set;
   (c) striking the inner spindle shaft along said spindle axis to induce an axially oscillating frequency;
   (d) measuring said oscillating frequency in said shaft or housing as it is affected by the degree of bearing preload of said at least one bearing set; and
   (e) comparing said measured induced frequency to a known frequency analysis for said type of spindle assembly which is correlated to varying bearing preloads, said comparison indicating the spindle bearing functionality prior to service.

4. The method as in claim 3, in which in step (e) said comparison is carried out to find the preload force of the spindle under test and determine if such tested preload force is within a designed range of preload forces.

5. The method as in claim 3, in which the said front bearing has (i) one or more rows of first roller bearings operating between inner and outer races, all with the same first bearing contact angle, ii) one or more rows of second roller bearings operating between inner and outer races, all with the same second bearing contact angle opposite and complementary to the first contact angle, and (iii) inner and outer spacer bushings separating said first and second roller bearing rows, said inner spacer bushing having a predefined offset gap relative to said outer spacer bushing to create spacing for axially compressing the inner races of said bearing sets and generate a preload force by incrementally deforming said roller bearings between said inner and outer races.

6. The method as in claim 5, in which said offset gap is created by grinding away the ends of said races or spacer bushings to an offset with tolerances on the order of approximately 0.0001 inch.

7. The method as in claim 3, in which said support is comprised of fabric or soft foam.

8. The method as in claim 3, in which said housing and shaft and bearing elements are comprised of metal.

* * * * *